United States Patent [19]

Cueman et al.

[11] 4,099,524
[45] Jul. 11, 1978

[54] SACRO-LUMBAR SUPPORT BELT

[75] Inventors: Glenn F. Cueman; Robert J. Becker, both of Warsaw, Ind.

[73] Assignee: Zimmer, U.S.A. Inc., Warsaw, Ind.

[21] Appl. No.: 840,700

[22] Filed: Oct. 11, 1977

Related U.S. Application Data

[63] Continuation of Ser. No. 629,475, Nov. 5, 1975, abandoned.

[51] Int. Cl.² .............................................. A61F 5/02
[52] U.S. Cl. .............................. 128/78; 128/DIG. 15
[58] Field of Search ................... 128/75, 78, DIG. 15

[56] References Cited

U.S. PATENT DOCUMENTS

| | | | |
|---|---|---|---|
| 3,013,561 | 12/1961 | Nelkin | 128/78 X |
| 3,096,760 | 7/1963 | Nelkin | 128/78 X |
| 3,399,669 | 9/1968 | Kaplan | 128/78 |
| 3,441,027 | 4/1969 | Lehman | 128/78 X |
| 3,452,748 | 7/1969 | Caprio | 128/78 |
| 3,561,434 | 2/1971 | Kilbey | 128/78 X |
| 3,561,436 | 2/1971 | Gaylord, Jr. | 128/78 X |
| 3,570,480 | 10/1968 | Stubbs | 128/78 |
| 3,717,143 | 2/1973 | Johnson | 128/78 |
| 3,797,483 | 3/1974 | Feldman | 128/DIG. 15 |
| 3,872,860 | 3/1975 | Noblitt | 128/DIG. 15 |
| 3,921,222 | 11/1975 | Hollman | 128/78 X |
| 3,927,665 | 12/1975 | Wax | 128/78 |

*Primary Examiner*—John D. Yasko
*Attorney, Agent, or Firm*—Richard H. Brink; David J. Mugford

[57] ABSTRACT

A sacro-lumbar support belt includes an outer face completely covered by a looped fabric and two elastic tightening panels, each panel rigidly coupled at one end to the outer face and having at its other end a hook means for releasably securing that end to the outer surface at any desired location. Pelvic traction straps with hook means at one end are releasably engageable on the belt outer face at any desired location.

5 Claims, 11 Drawing Figures

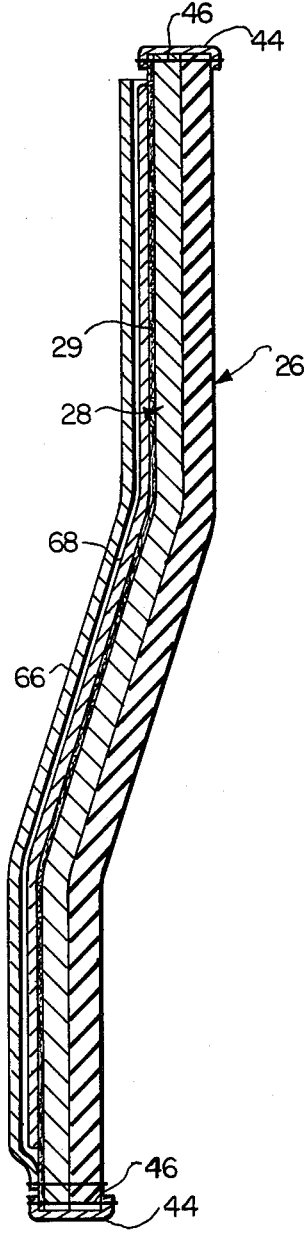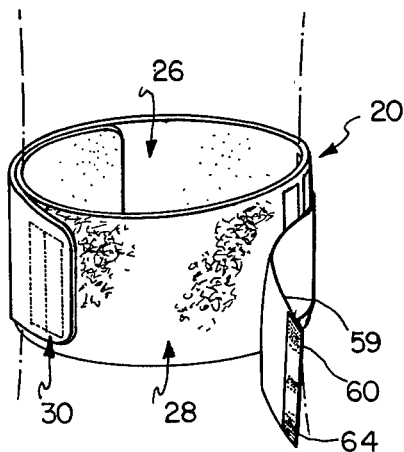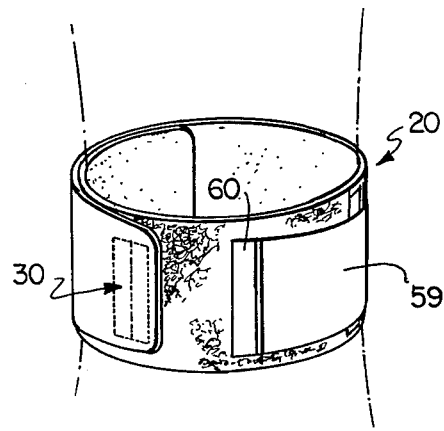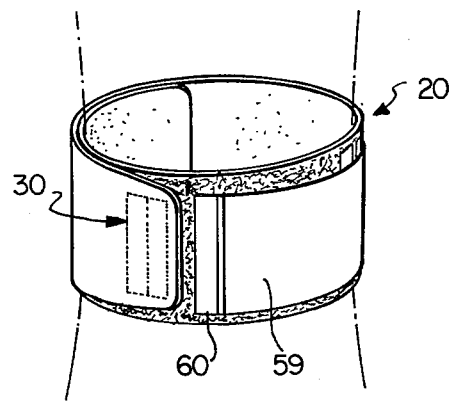

SACRO-LUMBAR SUPPORT BELT

This is a continuation of application Ser. No. 629,475, filed Nov. 5, 1975, now abandoned.

The present invention relates to a sacro-lumbar support belt and more particularly relates to a support belt with means for enhancing such support by tightening of the belt and with means for readily attaching pelvic traction straps to the belt.

Many prior art devices have been known for providing support to the lumbo-sacral area in the lower back; however, these known prior art devices suffer from two specific disadvantages. First, they are difficult to fit on the patient needing such a support since they are not readily adjustable, resulting in the requirement of keeping large inventories of support belts having various fixed sizes. Additionally, many of these belts do not provide sufficient support to the patient as necessary, and even if they do provide a minimum amount of support, such support is not readily variable.

In addition, many of the prior art sacro-lumbar support belts are not capable of readily receiving pelvic traction straps, which necessitates utilization of a separate, non-supporting, belt during traction.

Accordingly, it is a primary object of the present invention to provide a sacro-lumbar support belt which will be readily adjustable to a large range of sizes.

Another object is to provide a sacro-lumbar support belt which is capable of varying the support provided and providing a very high degree of support when necessary.

A further object of the present invention is to provide a sacro-lumbar support belt which is capable of readily receiving pelvic traction straps for use during traction, while providing sufficient support during such treatment.

A further object is to provide a sacro-lumbar support belt capable of receiving pelvic traction straps in any desired location with a small chance of separation of the traction straps from the belt during the traction process.

The foregoing objects are attained by providing a sacro-lumbar support belt comprising a waist encircling member, said member having top, bottom and two side edges and inner and outer faces, first means for securing said member about the waist of a person with said inner face positioned against the person, said outer face of said member being formed of looped fabric means for releasably engaging a hook means, second means located along said top and bottom edges for rendering said member substantially non-stretchable in the longitudinal direction, third means for tightening said member once it is secured about the person's waist, said third means including two elastic panels, each having a first end and a second end, fourth means for rigidly coupling said elastic panels at their first ends to said member outer face, and hook means located at each of said second ends for releasably engaging said looped fabric means on said outer face so said elastic panel second ends are securable to said outer face at any desired location therealong.

Additionally, the sacro-lumbar support belt includes at least one pelvic traction strap which includes an elongated non-stretchable member, means for securing one end of said elongated member to a traction weight, and strap hook means for releasably engaging the other end of said elongated member to said looped fabric means on said outer face.

Other objects, advantages and salient features of the present invention will become apparent from the following detailed description, which, taken in conjunction with the annexed drawings, discloses preferred embodiments of the present invention.

Referring now to the drawings which form a part of this original disclosure:

FIG. 5 is a side elevational view in section taken along lines 5—5 of FIG. 1 showing a pocket located on the belt with a metal stay located therein;

FIG. 6 is a perspective view of the sacro-lumbar support belt shown in FIG. 1 secured around the waist of the wearer with the tensioning means in a relaxed position;

FIG. 7 is a view similar to that shown in FIG. 6 but with the tensioning means in a stretched position having one end secured to the outer face of the belt providing a certain degree of tensioning;

FIG. 8 is a view similar to that shown in FIG. 7 but with the tensioning means stretched further around the belt, thereby providing a higher degree of tightening;

Figure 1:
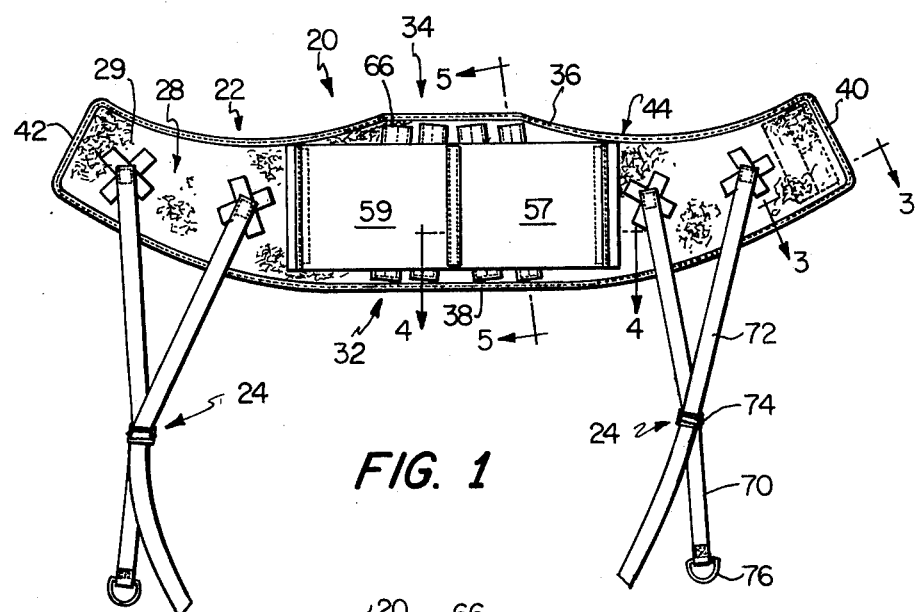
FIG. 1 is a front elevational view of the sacro-lumbar support belt in accordance with the present invention having two pelvic traction straps releasably connected thereto.
Figure 2:
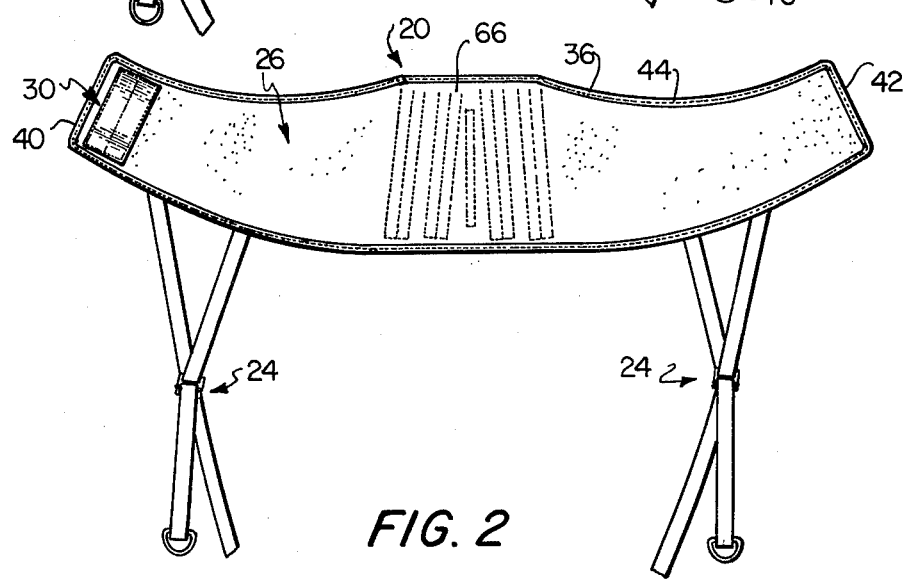
FIG. 2 is a rear elevational view of the device shown in FIG. 1.

Referring now to the drawings in further detail, as shown in FIGS. 1 and 2, the sacro-lumbar support belt 20 includes a waist encircling member 22 and two pelvic traction straps 24. The waist encircling member includes an inner portion 26, an outer portion 28, a securing assembly 30, a tensioning assembly 32 and a stay support assembly 34.

The inner portion 26 is formed of urethane foam and the outer portion 28 is formed of a brushed nylon pile having a surface of looped fabric 29 completely covering the outer face of the outer portion, these inner and outer portions forming a laminate by being coupled together by an adhesive process or flame process. The laminate so formed is slightly stretchable both in the longitudinal and transverse directions.

Figure 3:
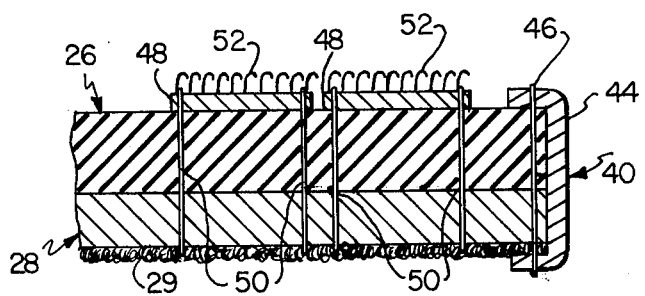
FIG. 3 is a top plan view in section taken along lines 3—3 of FIG. 1 showing the means for securing the belt around the waist of the wearer.

Stitched about the top edge 36, the bottom edge 38, the first side edge 40 and second side edge 42 of the waist encircling member 22 is a non-stretchable fabric 44 which renders such member substantially non-stretchable in the longitudinal direction thereof. As shown more clearly in FIGS. 3 and 5, the fabric covers the outside edges of the inner portion 26 and the outer portion 28 and extends inwardly therefrom where it is stitched firmly to the laminate formed by these portions. As seen in FIGS. 3 and 5, this stitching is identified by character numeral 46 which passes through the overlapping portions of the fabric as well as the edges of the inner and outer portions forming the waist encircling member 22.

As best seen in FIGS. 2 and 3, the securing assembly 30 is formed from two pads 48 secured to the inner portion 26 adjacent the first side edge 40 by stitching 50, these pads 48 having hooks 52 extending therefrom. These hooks are of the type which will releasably engage with the looped fabric on the outer face of the outer portion 28, such releasable securing mechanism being substantially the same as that sold under the trademark VELCRO as described in U.S. Pat. No. 3,009,235, issued on Nov. 21, 1961 to G. De Mestral.

Figure 4:
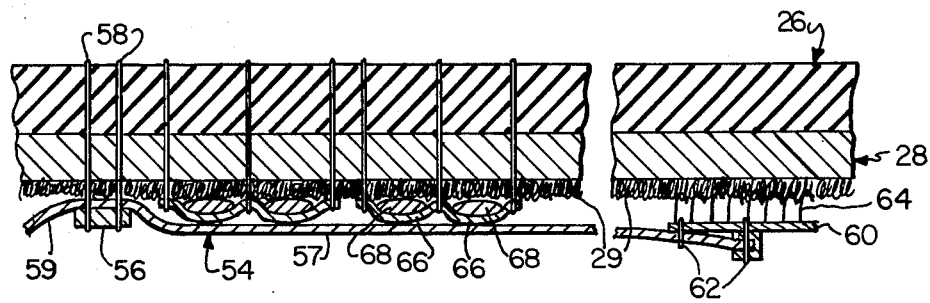
FIG. 4 is a top plan view in section taken along lines 4—4 of FIG. 1 showing the tensioning means for varying the tightness of the sacro-lumbar belt.

The tensioning assembly 32, shown most clearly in FIGS. 1 and 4, comprises a rectangularly shaped elastic panel 54 secured at its midpoint to the outer portion 28 of the waist encircling member 22 by means of a pad 56 overlying the panel and coupled to the member 22 by means of a pad 56 overlying the panel and coupled to the member 22 by stitching 58. The elastic panel 54 is stretchable in both its longitudinal and transverse directions and has a relaxed length equal to approximately one-half the overall longitudinal length of the waist encircling member 22. Panel 54 is divided by pad 56 into a right side panel 57 and a left side panel 59. On the distal ends of each of the panels 57 and 59 is a pad 60 stitched thereto via stitching 62, the pad 60 carrying on its side facing the outer portion 28 a series of hooks 64 similar to those contained on pads 48 in the securing assembly 30. As is evident from FIG. 4, these hooks 64 can be releasably engaged with the looped fabric outer face of the outer portion 28. While elastic panel 54 is shown as one integral piece, it is contemplated that two separate elastic panels can be utilized as long as each is rigidly secured to the waist encircling member 22 in a fashion similar to that provided by pad 56 and stitching 58, as shown in FIG. 4.

Referring again to FIGS. 1, 2 and 5, the stay support assembly 34 is shown comprising a plurality of pockets 66 stitched to the outer portion 28 with a plurality of metal stays 68 carried inside the pockets. As shown best in FIG. 2, there is utilized four sets of two pockets 66, with each set being capable of receiving two of the metal stays 68. As seen in FIG. 5, the stays 68 are preferably bent in two places to conform with the contour of the lumbo-sacral area of the person's lower back region.

Referring now to FIGS. 6, 7 and 8, utilization of the sacro-lumbar support belt around a person's waist is illustrated. Thus, as shown in FIG. 6, the waist encircling member 22 is wrapped around the waist with the hooks 52 on the securing assembly 30 grasping the looped fabric on the outer face of the outer portion 28 so as to secure the member 22 in the proper position. Since the entire outer face of the outer portion 28 contains looped fabric which is releasably engageable with the hooks 52, the belt 20 illustrated can be adjusted to a numerous number of waist sizes. As shown in FIG. 6, the tensioning assembly 32 has its distal ends unconnected to the outer portion 28 so that the belt 20 provides support merely from its being wrapped around the person's waist. However, in order to increase the support provided to the person wearing the belt, the distal ends of the elastic panel 54 having pads 60 and hooks 64 thereon can be pulled towards the front of the wearer, thereby stretching the elastic panel, and secured at any desired position by means of engagement of the hooks 64 with the looped fabric on the outer portion 28 of the belt. One such position is shown in FIG. 7, with another position being shown in FIG. 8, the latter providing an increase in support to the wearer because of the additional stretching of the elastic panels 54. Because the hooks 64 are engageable with the outer portion 28 looped fabric outer face in any position, the adjustment of the support by the tensioning assembly 32 is infinitely variable and therefore provides an extremely wide range of support to the person wearing the belt 20, including a very high degree of support when the elastic panel 54 is stretched to substantially the ends of the belt 20.

Figure 9:
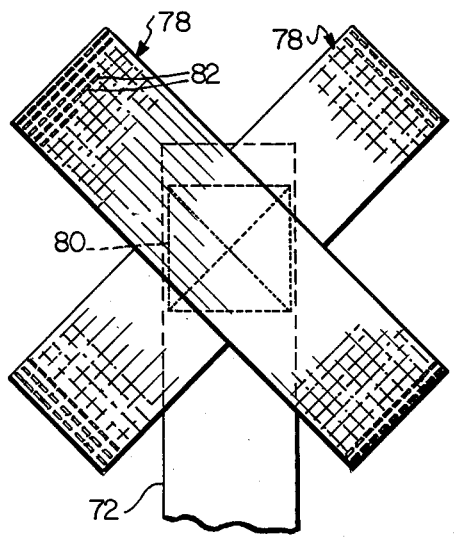
FIG. 9 is an elevational view of the underside of one of the traction straps shown coupled to the belt in FIG. 1.

Turning now to FIGS. 1, 2 and 9, it is apparent that the sacro-lumbar support belt 20 can additionally be utilized during a traction process by the expedient addition thereto of the pelvic traction straps 24.

Each pelvic traction strap 24 is comprised of a straight elongated, non-stretchable member 70 and a curved, non-stretchable member 72 coupled to the straight member by means of a buckle 74. At the free end of the straight member 70 is a curved ring 76 for connection with a traction tensioning weight or similar device. The curved member 72 has at each distal end a pair of crossed pads 78 stitched thereto by means of stitching 80. As best seen in FIG. 9, the sides of the pads 78 facing the outer portion 28 of the belt 20 contains a plurality of rows of hooks 82 which are similar to those in the securing assembly 30 and are therefore releasably engageable with the looped fabric outer face of the outer portion 28. Thus, the pelvic traction straps 24 can be releasably engaged with the belt 20 in any desired position along the outer portion 28 since that portion is completely covered with the looped fabric.

Figure 11:
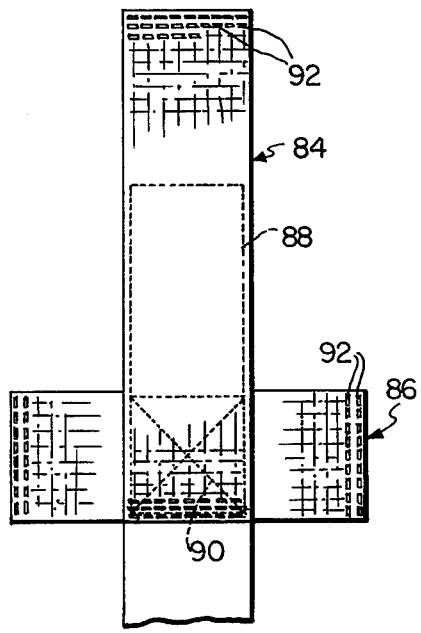
FIG. 11 is an elevational view showing the details of the modified traction strap shown in FIG. 10.
Figure 10:
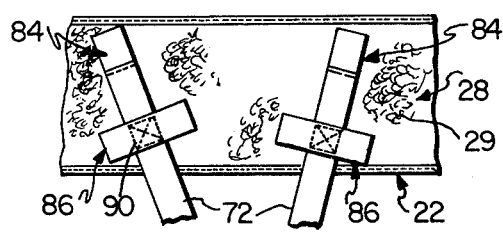
FIG. 10 is an elevational view of a modified traction strap coupled to the belt shown in FIG. 1.

Referring now to FIGS. 10 and 11, a modified connection of the pelvic traction straps is shown in which pad 84 is stitched via stitching 88 to the end of a curved member 72 along the longitudinal line of that member and pad 86 is stitched via stitching 90 perpendicularly to the pad 84, so that these pads 84 and 86 are in a T-shaped configuration. Each of these pads has a plurality of rows of hooks 92 similar to those described regarding the traction strap shown in FIG. 9 for releasable engagement in any desired position along the outer face of the outer portion 28.

While various advantageous embodiments have been chosen to illustrate the invention, it will be understood by those skilled in the art that various changes and modifications can be made therein without departing from the scope of the invention as defined in the appended claims.

What is claimed is:

1. A sacro-lumbar support belt comprising:
a waist encircling member,
said member having top, bottom and two side edges, and inner and outer faces;
said outer face of said member being formed entirely of brushed nylon pile;
said inner face of said member being formed of urethane foam and having hook means located adjacent one end of said member, for releasably engaging said brushed nylon pile on said outer face to secure said member about the waist of a person with said inner face positioned against the person;
non-stretchable fabric secured along said top and bottom edges by stitching for rendering said member substantially non-stretchable in the longitudinal direction;
non-stretchable fabric secured along said two side edges and interconnecting said non-stretchable fabric on said top and bottom edges;

a plurality of pockets secured to said outer face, said pockets extending transversely of said waist encircling member between said top and bottom edges;
a plurality of stays receivable in said pockets;
means for tightening said member once it is secured about the person's waist,
said means including
two rectangularly-shaped elastic panels, each having a first end and a second end and being substantially as wide as said waist encircling member,
means for rigidly coupling said elastic panels at their first ends to said member outer face, and
hooks means, located at each of said second ends, for releasably engaging said brushed nylon pile on said outer face so said elastic panel second ends are securable to said outer face at any desired location therealong.

2. A belt according to claim 1 wherein
each of said elastic panels has a relaxed length between said first and second ends thereof which is substantially equal to one-fourth the length of said waist encircling member between said two side edges.

3. A belt according to claim 1 and further including at least one pelvic traction strap, said strap including
an elongated, non-stretchable member,
means for securing one end of said elongated member to a traction weight, and
strap hook means for releasably engaging the other end of said elongated member to said looped fabric means on said outer face.

4. A belt according to claim 3 wherein said strap hooks means has a T-shaped configuration.

5. A belt according to claim 3 wherein said strap hook means has an X-shaped configuration.

* * * * *